US012033321B2

(12) United States Patent
Bhattacharya et al.

(10) Patent No.: US 12,033,321 B2
(45) Date of Patent: Jul. 9, 2024

(54) AUGMENTATION OF OPTICAL COHERENCE TOMOGRAPHY IMAGE OF EYE BASED ON LEARNING MODULES

(71) Applicant: Alcon Inc., Fribourg (CH)

(72) Inventors: Sinchan Bhattacharya, Denton, TX (US); Hyo Won Choi, Keller, TX (US); Ramesh Sarangapani, Coppell, TX (US); Bryan Stanfill, Mansfield, TX (US)

(73) Assignee: Alcon Inc., Fribourg (CH)

( * ) Notice: Subject to any disclaimer, the term of this patent is extended or adjusted under 35 U.S.C. 154(b) by 441 days.

(21) Appl. No.: 17/507,644

(22) Filed: Oct. 21, 2021

(65) Prior Publication Data

US 2022/0198654 A1 Jun. 23, 2022

Related U.S. Application Data

(60) Provisional application No. 63/128,027, filed on Dec. 19, 2020.

(51) Int. Cl.
*G06K 9/00* (2022.01)
*A61F 9/008* (2006.01)
*G06T 7/00* (2017.01)

(52) U.S. Cl.
CPC ............ *G06T 7/0012* (2013.01); *A61F 9/008* (2013.01); *A61F 2009/00851* (2013.01); *G06T 2207/10056* (2013.01); *G06T 2207/10101* (2013.01); *G06T 2207/10132* (2013.01); *G06T 2207/20081* (2013.01); *G06T 2207/20084* (2013.01); *G06T 2207/30041* (2013.01)

(58) Field of Classification Search
CPC . G06T 2207/10101; G06T 2207/20081; G06T 7/0012; A61F 2009/00851
See application file for complete search history.

(56) References Cited

U.S. PATENT DOCUMENTS

| | | |
|---|---|---|
| 2020/0229870 A1 | 7/2020 | Sarangapani et al. |
| 2023/0084284 A1* | 3/2023 | Burwinkel ............ G06N 3/045 382/131 |

OTHER PUBLICATIONS

Halupka, Kerry J., et al. "Retinal optical coherence tomography image enhancement via deep learning." Biomedical optics express 9.12 (2018): 6205-6221. (Year: 2018).*

(Continued)

*Primary Examiner* — Emily C Terrell
*Assistant Examiner* — Owais Iqbal Memon (57) ABSTRACT

A system and method for augmenting an original OCT (optical coherence tomography) image includes a controller having a processor and a tangible, non-transitory memory on which instructions are recorded. The system includes one or more learning modules selectively executable by the controller. The learning modules are trained by a training network with a training dataset having a plurality of training ultrasound bio-microscopy images and respective training OCT images. Execution of the instructions by the processor causes the controller to obtain the original OCT image, captured through an OCT device. The controller is configured to generate an augmented OCT image based in part on the original OCT image, by executing the (trained) learning modules. The augmented OCT image at least partially extends a peripheral portion of the original OCT image.

19 Claims, 4 Drawing Sheets

(56) References Cited

OTHER PUBLICATIONS

Kepp, Timo, et al. "Segmentation of retinal low-cost optical coherence tomography images using deep learning." Medical Imaging 2020: Computer-Aided Diagnosis. vol. 11314. SPIE, Mar. 16, 2020. (Year: 2020).*

Jun-Yan Zhu et al: "Unpaired Image-to-Image Translation usingCycle-Consistent Adversarial Networks", arxiv.org, Cornell University Library, 201 Olin Library Cornell University Ithaca, NY 14853, Mar. 30, 2017 (Mar. 30, 2017), XP080753281.

Kugelman Jason et al: "Constructing Synthetic Chorio-Retinal Patches using Generative Adversarial Networks",2019 Digital Image Computing: Techniquesand Applications (DICTA), IEEE, Dec. 2, 2019 (Dec. 2, 2019), pp. 1-8, XP033683122, DOI: 10.1109/DICTA47822.2019.8946089[retrieved on Dec. 30, 2019].

Kugelman J et al: "Dual image and mask synthesis with GANs for semantic segmentation in optical coherence tomography", Proceedings of the 2020 Digital Imagecomputing: Techniques and Applications (DICTA) IEEE Piscataway, NJ, USA,, Nov. 29, 2020 (Nov. 29, 2020), pp. 1-8, XP002804910, ISBN: 978-1-7281-9108-9.

Seebock Philipp et al: Using Cyclegans for Effectively Reducing Image Variability Across OCT Devices and Improving RetinalFluid Segmentation, 2019 IEEE 16th International Symposium on Biomedical Imaging (ISBI 2019), IEEE, Apr. 8, 2019 (Apr. 8, 2019), pp. 605-609, XP033576339, DOI: 10.1109/ISBI.2019.8759158.

Wanichwecharungruang Boonsong et al: "Deep Learning for Anterior Segment Optical Coherence Tomography to Predictthe Presence of Plateau Iris", Translational Vision Science & Technology, vol. 10, No. 1, Jan. 6, 2021 (Jan. 6, 2021), p. 7,XP055874039, US, ISSN: 2164-2591.

Janssens Katleen et al: To Study and Determine the Role of Anterior Segment Optical Coherence Tomography and Ultrasound Biomicroscopy in Corneal and Conjunctival Tumors, Journal of Ophthalmology, [Online] vol. 2016, 2016, pp. 1-11, XP055874045, US.

* cited by examiner

AUGMENTATION OF OPTICAL COHERENCE TOMOGRAPHY IMAGE OF EYE BASED ON LEARNING MODULES

INTRODUCTION

The disclosure relates generally to augmentation of an optical coherence tomography image of an eye, based on one or more learning modules. Optical coherence tomography ("OCT") is a noninvasive imaging technology using low-coherence interferometry to generate high-resolution images of ocular structure. OCT imaging functions partly by measuring the echo time delay and magnitude of backscattered light. Images generated by OCT are useful for many purposes, such as identification and assessment of ocular diseases. OCT images are frequently taken prior to cataract surgery, where an intraocular lens is implanted into a patient's eye. An inherent limitation of OCT imaging is that the illuminating beam cannot penetrate across the iris. Hence posterior regions of the eye, such as the crystalline lens structure behind the iris, may not be properly visualized.

SUMMARY

Disclosed herein is a system and method for augmenting an original optical coherence tomography ("OCT" hereinafter) image of an eye. The system includes a controller having a processor and a tangible, non-transitory memory on which instructions are recorded. The system includes one or more learning modules ("one or more" omitted henceforth) selectively executable by the controller. The learning modules are trained by a training network with a training dataset having a plurality of training ultrasound bio-microscopy images and respective training OCT images. Execution of the instructions by the processor causes the controller to obtain the original OCT image, captured through an OCT device. The controller is configured to generate an augmented OCT image based in part on the original OCT image, by executing the (trained) learning modules. The augmented OCT image at least partially extends a peripheral portion of the original OCT image. In other words, the system enables reconstruction of missing information from the original OCT image.

The peripheral portion may be posterior to an iris of the eye such that the augmented OCT image enables visualization of one or more structures posterior to the iris. The controller may be configured to obtain at least one lens parameter based on the augmented OCT image. The lens parameters may include a lens diameter and/or a lens capsule profile. The controller may be configured to select an intraocular lens for the eye based in part on the lens parameters. The OCT device may include an array of laser beams for illuminating the eye.

In some embodiments, the respective training OCT images are correlated to the plurality of training ultrasound bio-microscopy images, such that the respective training OCT images and the plurality of training ultrasound bio-microscopy images form paired sets (i.e., images of the same eye). The learning module may include a generator trained to generate respective synthesized OCT images based in part on the respective training OCT images. The training network may be a generative adversarial network having a discriminator. The discriminator is adapted to distinguish between the plurality of training ultrasound bio-microscopy images and the respective synthesized OCT images.

In some embodiments, the respective training OCT images are not correlated (i.e., are images of different eyes) to the plurality of training ultrasound bio-microscopy images, such that the respective training OCT images and the plurality of training ultrasound bio-microscopy images form unpaired sets. The training network may be a generative adversarial network having a first discriminator and a second discriminator. The learning modules may include a first generator and a second generator. The augmented OCT image may be generated by executing the first generator and the second generator in sequence, with the first generator being adapted to translate the original OCT image of the eye into a respective synthesized UBM image and the second generator being adapted to translate the respective synthesized UBM image into the augmented OCT image.

The training network may be configured to execute a forward training cycle with the first generator, the second generator and the first discriminator. Here, a first training OCT image is inputted into the first generator, with the first training OCT image being selected from the respective training OCT images. The first generator to adapted to translate the first training OCT image into a first synthesized ultrasound bio-microscopy image. The second generator is adapted to translate the first synthesized ultrasound bio-microscopy image into a second synthesized OCT image. The first discriminator is adapted to distinguish between the first synthesized ultrasound bio-microscopy image and the plurality of training ultrasound bio-microscopy images in the forward training cycle. The training network incorporates a first loss function minimizing differences between the first training OCT image and the second synthesized OCT image.

The training network may be further configured to execute a reverse training cycle with the first generator, the second generator and the second discriminator. Here, a second training ultrasound bio-microscopy image is inputted into the second generator, the second training ultrasound bio-microscopy image being selected from the plurality of training ultrasound bio-microscopy images. The second generator is configured to translate the second training ultrasound bio-microscopy image into a third synthesized OCT image. The first generator is configured to translate the third synthesized OCT image into a fourth synthesized ultrasound bio-microscopy image. The second discriminator is adapted to distinguish between the third synthesized OCT image and the respective training OCT images in the reverse training cycle. The training network may incorporate a second loss function minimizing differences between the second training ultrasound bio-microscopy image and the fourth synthesized ultrasound bio-microscopy image.

A method is disclosed herein for augmenting an original optical coherence tomography ("OCT") image of an eye with a system having a controller with at least one processor and at least one non-transitory, tangible memory. The method includes configuring the controller to selectively execute one or more learning modules. The learning modules are trained, via a training network, with a training dataset having a plurality of training ultrasound bio-microscopy images and respective training OCT images. The method includes capturing the original OCT image of the eye, via an OCT device. An augmented OCT image is generated based in part on the original OCT image by executing the one or more learning modules. The augmented OCT image at least partially extends a peripheral portion of the original OCT image.

In some embodiments, the peripheral portion is located posterior to an iris of the eye such that the augmented OCT image enables visualization of one or more structures posterior to the iris. The method may include obtaining at least one lens parameter based on the augmented OCT image, the lens parameter including a lens diameter and/or a lens capsule profile. An intraocular lens may be selected based in part on the lens parameter.

Capturing the original OCT image of the eye may include illuminating the eye with an array of laser beams, via the OCT device. The method may include composing the training dataset with paired sets (i.e., images of the same eye) of the plurality of training ultrasound bio-microscopy images and respective training OCT images. Alternatively, the method may include composing the training dataset with unpaired sets (i.e., images of different eyes) of the plurality of training ultrasound bio-microscopy images and respective training OCT images.

The above features and advantages and other features and advantages of the present disclosure are readily apparent from the following detailed description of the best modes for carrying out the disclosure when taken in connection with the accompanying drawings.

DETAILED DESCRIPTION

Figure 1:
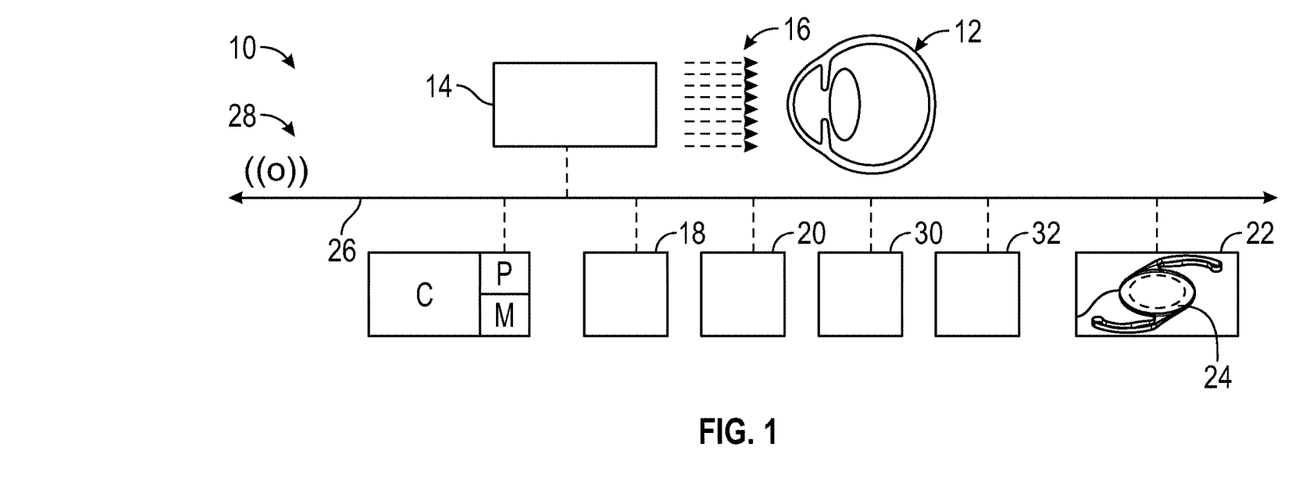
FIG. 1 is a schematic illustration of a system for augmenting an original optical coherence tomography ("OCT") image of an eye, the system having a controller and one or more learning modules.

Referring to the drawings, wherein like reference numbers refer to like components, FIG. 1 schematically illustrates a system 10 for augmenting an original optical coherence tomography image of an eye 12, captured via an optical coherence tomography image ("OCT" hereinafter) device 14. The OCT device 14 may employ an array of laser beams 16 for illuminating the eye 12. The array of laser beams 16 may cover the span or width of the eye 12. In one example, the OCT device 14 is an anterior segment high definition OCT imaging device. It is to be understood that the OCT device 14 may take many different forms and include multiple and/or alternate components.

Referring to FIG. 1, the system 10 includes a controller C having at least one processor P and at least one memory M (or non-transitory, tangible computer readable storage medium) on which instructions are recorded for executing method 100 for augmenting the original OCT image 200 of the eye 12. Method 100 is shown in and described below with reference to FIG. 2.

Figure 3:
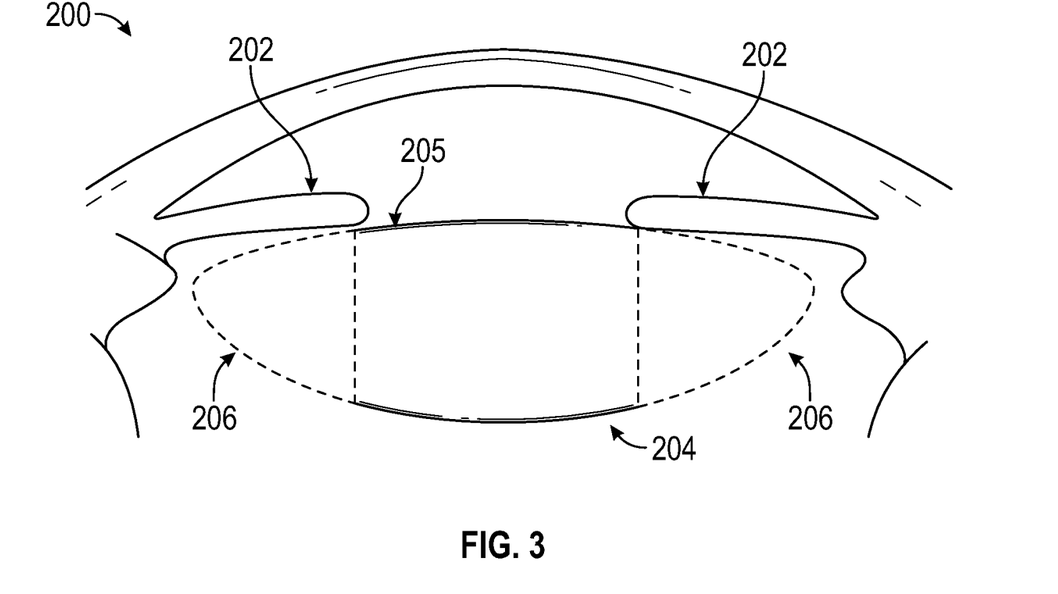
FIG. 3 is a schematic illustration of an example original OCT image of the eye.

An example of an original OCT image 200 is schematically shown in FIG. 3 and described below. In the example shown, the original OCT image 200 displays an anterior segment view. Referring to FIG. 3, the original OCT image 200 shows the iris 202, lens 204 and pupil 205. OCT imaging does not capture the peripheral portion 206 of the lens 204 that is behind the iris 202. This is because the illuminating lasers used in OCT imaging cannot penetrate across the iris 202. However, OCT imaging techniques provide high resolution and a non-contact scanning method that is convenient in terms of patients' compliance and comfort in daily clinical settings. For example, the OCT imaging is performed in the sitting position, takes a relatively short amount of time, and does not involve the use of eyecups or coupling medium. As described below, the system 10 obtains one or more learning modules 18 ("one or more" omitted henceforth) that are trained to extrapolate the original OCT image 200 captured by the OCT device 14 and reconstruct an augmented OCT image showing the peripheral portion 206. The system 10 enables reconstruction of the complete image of the lens 204 based on the original OCT image 200.

Figure 4:
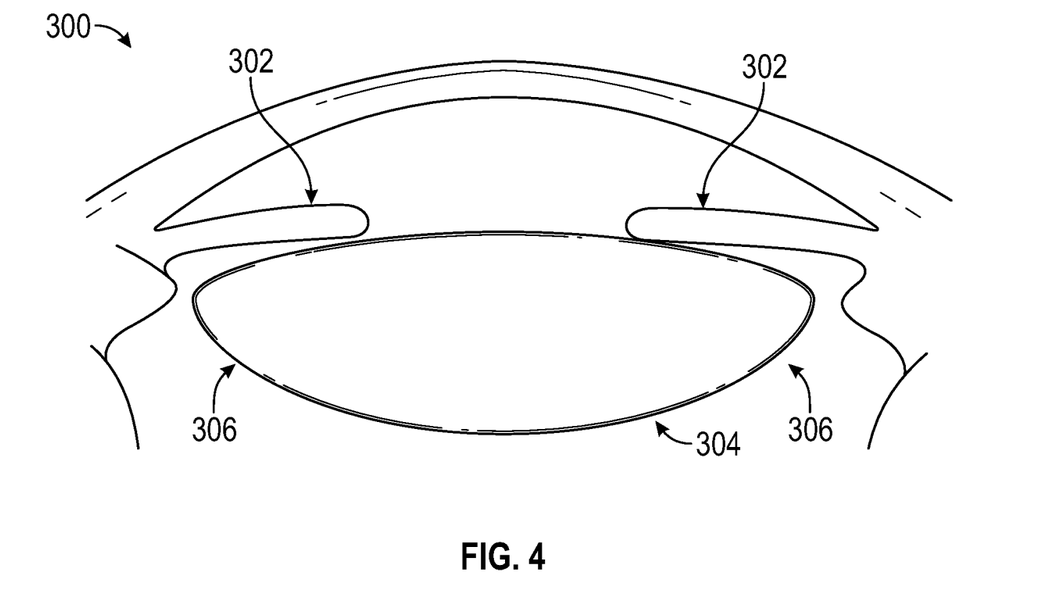
FIG. 4 is a schematic illustration of an ultrasound bio-microscopy (UBM) image of an eye.

Referring to FIG. 1, the controller C is specifically programmed to selectively execute the learning modules 18, which may be embedded in the controller C or may be stored elsewhere and accessible to the controller C. Referring to FIG. 1, the learning modules 18 are trained by a training network 20 with a training dataset having a plurality of training ultrasound bio-microscopy images (and respective training OCT images described below). An example of a training ultrasound bio-microscopy image 300 is schematically shown in FIG. 4. The training ultrasound bio-microscopy image 300 shows the iris 302 and lens 304. The training ultrasound bio-microscopy image 300 also shows the peripheral portion 306 of the lens 304. Ultrasound bio-microscopy images are capable of capturing the entire crystalline lens structure, but at a lower resolution compared to images obtained by OCT imaging. However, ultrasound bio-microscopy imaging is less convenient for the patient. For example, ultrasound bio-microscopy imaging requires longer image acquisition times, a skilled operator and a plastic or silicone eyecup to hold a coupling medium.

Figure 5:
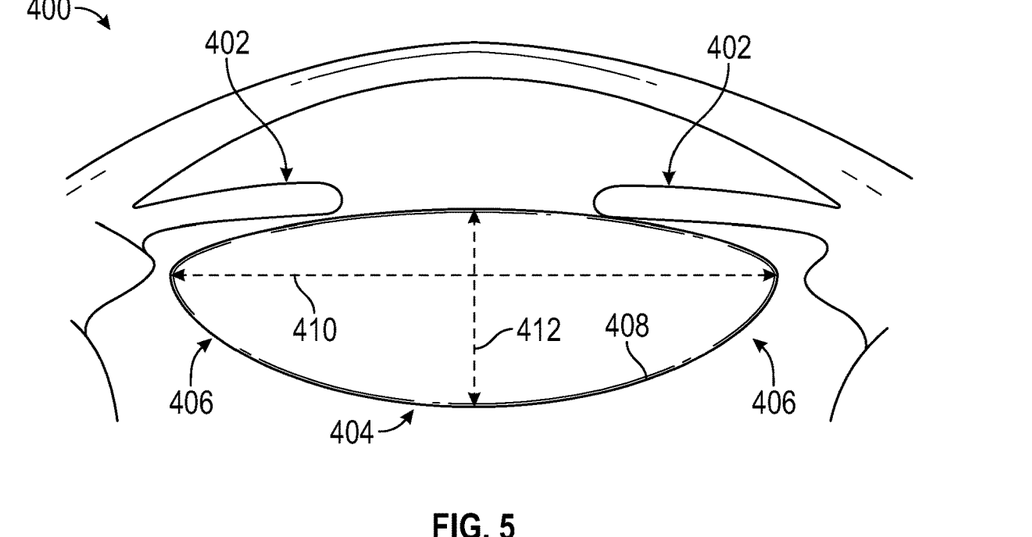
FIG. 5 is a schematic view of an augmented OCT image of the eye.

The controller C is configured to generate an augmented OCT image based in part on the original OCT image 200 by executing one or more learning modules 18. An example of an augmented OCT image 400 is schematically shown in FIG. 5 and described below. The augmented OCT image 400 illustrates the iris 402 and lens 404. The augmented OCT image 400 at least partially extends a peripheral portion 406 of the original OCT image. The peripheral portion 406 is posterior to the iris 402 such that visualization of one or more structures posterior to the iris 402 is achieved.

The training network 20 of FIG. 1 leverages convolutional neural network (CNN)-based deep learning techniques to augment the original OCT image 200. The training network 20 may incorporate a generative adversarial network (GAN). In one embodiment, training network 20 incorporates a cycle generative adversarial network (cycle-GAN).

The controller C is configured to obtain at least one lens parameter based on the augmented OCT image 400. Referring to FIG. 4, the lens parameters may include a lens capsule profile 408, lens diameter 410 and thickness 412 of the lens 404 along the lens diameter 410. The lens parameters may be outputted to a lens selection module 22 for selecting an intraocular lens 24 for implantation into the eye 12. A full image of the preoperative crystalline lens structure is valuable for selecting an appropriate power for an intraocular lens 24 during pre-operative assessments for cataract surgery. This information is particularly useful for intraocular lenses 24 that are accommodative in nature, as their functional performance has been observed to be correlated to the lens diameter 410. Additionally, the lens capsule profile 408 may be employed to estimate the likely position of the intraocular lens 24 post-operatively.

The various components of the system 10 of FIG. 1 may communicate via a short-range network 26 and/or a long-range network 28. The short-range network 26 may be a bus implemented in various ways, such as for example, a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data connection. Referring to FIG. 1, the long-range network 28 may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

Figure 2:
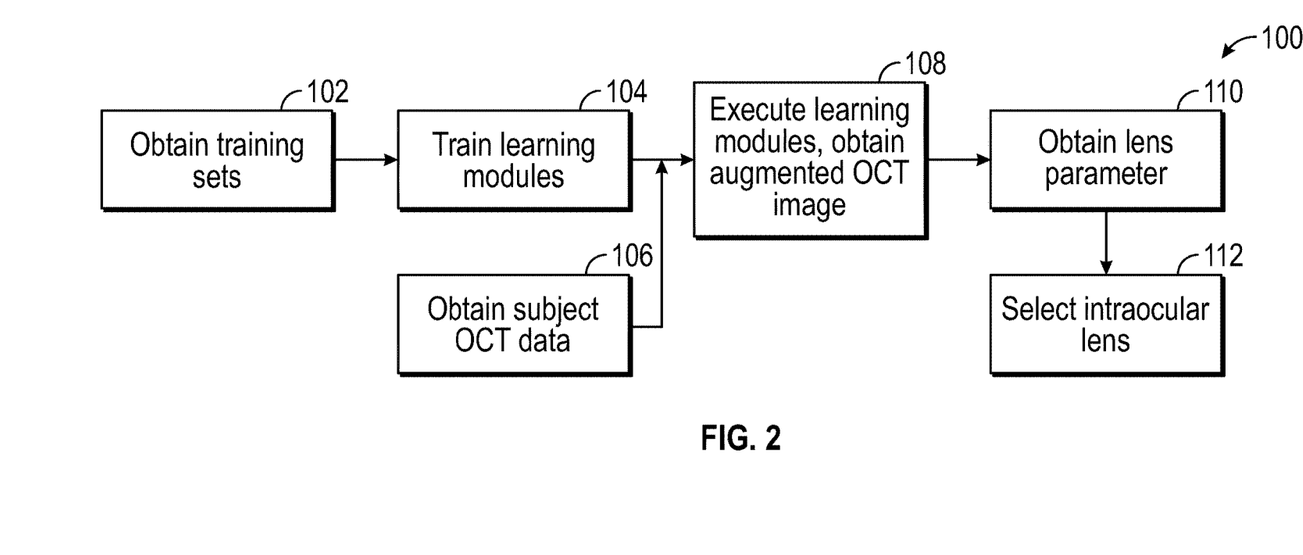
FIG. 2 is a schematic flowchart for a method executable by the controller of FIG. 1.

Referring now to FIG. 2, a flow chart of method 100 executable by the controller C of FIG. 1 is shown. Method 100 need not be applied in the specific order recited herein and some blocks may be omitted. The memory M can store controller-executable instruction sets, and the processor P can execute the controller-executable instruction sets stored in the memory M.

Per block 102 of FIG. 2, the controller C is configured to collect one or more training datasets, from one or more facilities or clinical sites located all over the world. The controller C may be in communication with the facilities via short-range network 26 and/or a long-range network 28. Referring to FIG. 1, the system 10 may include a data management module 30 having a computerized data management system able to store information from the respective electronic medical records of the facilities. The data management module 30 may be configured to collect the training dataset from the facilities and provide them to the controller C.

The training dataset may include images taken from a large number of patients. In some embodiments, the training dataset further includes paired sets of data, i.e., respective training OCT images that are correlated to the plurality of training ultrasound bio-microscopy images by being of the same eye. In other embodiments, the training dataset further includes unpaired sets of data, i.e., respective training OCT images that are not correlated (taken of different eyes) to the plurality of training ultrasound bio-microscopy images. The training datasets may be stratified based on demographic data, patients with similar-sized dimensions of eyes or other health status factors.

Per block 104 of FIG. 2, the method 100 includes training the learning modules with the training dataset from block 102, via the training network 20. Two embodiments of training processes are described below. It is to be understood that the system 10 is not limited to a specific deep neural network methodology. The reconstruction of missing information from the original OCT image 200 may be assisted by other deep neural network methodologies available to those skilled in the art.

In a first embodiment, the training network 20 incorporates a deep learning architecture, such as a generative adversarial network (GAN), for training a generator G* for image synthesis, coupled with a discriminator D*. An example of the first embodiment is described below with respect to FIG. 6. The discriminator D* is trained directly on real and generated images and is responsible for classifying images as real or fake. The generator G* is not trained directly and instead is trained via the discriminator D*.

Figure 6:
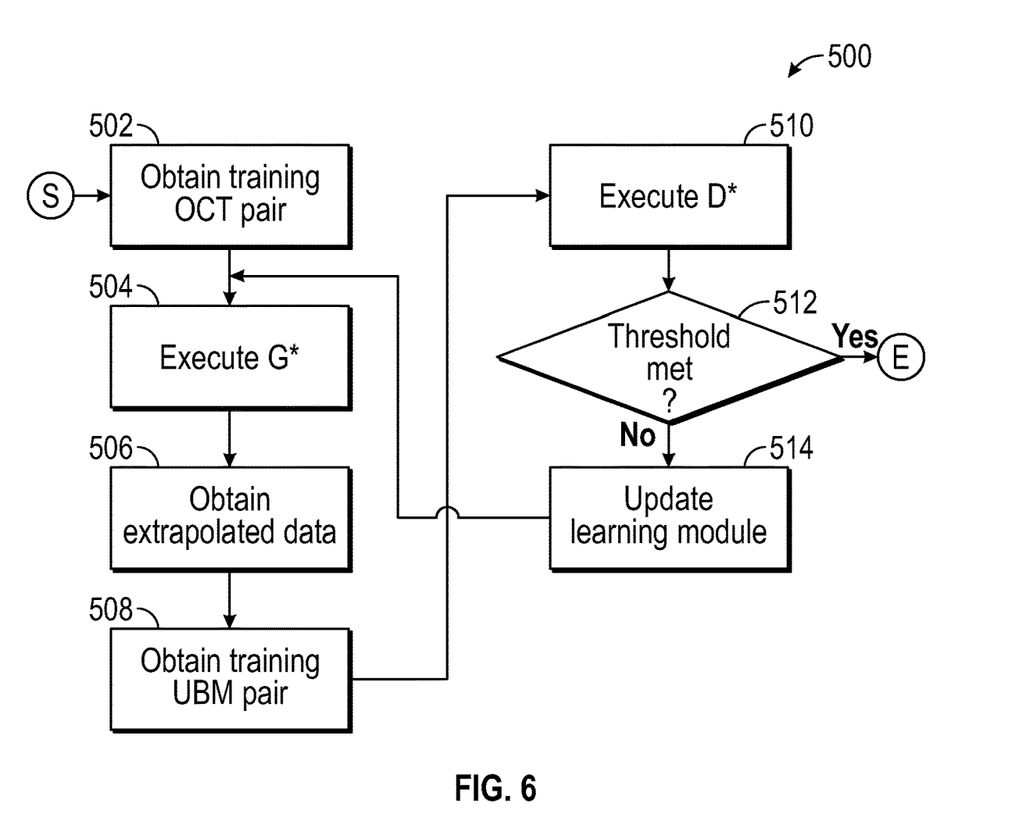
FIG. 6 is a schematic flowchart for an example training method for the learning modules of FIG. 1, in accordance with a first embodiment.

Referring to FIG. 6, a training method 500 is shown, which may be executed by the controller C. Per block 502, a training OCT image is obtained. In this embodiment, the training dataset includes paired sets of data, with paired OCT and ultrasound bio-microscopy images, taken of the same patient. Per block 504 of FIG. 6, the training method 500 includes executing the generator G*. Per block 506 of FIG. 6, the generator G* generates a synthesized ultrasound bio-microscopy image based in part on the respective training OCT images, extrapolating the data obtained in block 502. The training ultrasound bio-microscopy image that pairs with the training OCT image (obtained in block 502) is retrieved in block 508.

Per block 510 of FIG. 6, the training method 500 includes executing discriminator D*. The discriminator D* is used to "judge" the output of the generator G* and determine whether the output (the synthesized ultrasound bio-microscopy image of block 506) is close enough to the "real" training data (training ultrasound bio-microscopy image of block 508). The comparison is done through image to image. For example, the loss function may minimize the difference between intensity of individual pixels between the two images. The Generator G* attempts to create a synthesized ultrasound bio-microscopy image that is as close to "real" training data (training ultrasound bio-microscopy image of block 508) as possible. Thus, the discriminator D* is learned to provide a loss function for the generator G*.

The training method 500 then proceeds to block 512 to determine if a predefined threshold is met. In one example, the predefined threshold is met when the difference in respective intensity of pixels (registered to be at the same physical location) between the two images is within a predefined value, such as for example, 10%. In another example, the predefined threshold is met when the difference in lens diameter between the two images is within a predefined value. Additionally, the predefined threshold may be met when the difference in other parameters related to the lens, such as end capsule height, between the two images is within a predefined value. The predefined value may be within 5% or 5 millimeters. If the predefined threshold is met, the training method 500 exits. If the predefined threshold is not met, the training method 500 proceeds to block 512, where the learning module 18 is updated and the training method 500 loops back to block 504. The training process occurs in a closed loop or iterative fashion, with the learning modules 18 being trained until a certain criteria is met. In other words, the training process continues until the discrepancy between the network outcome and ground truth reaches a point below a certain threshold. As the loss function related to the training dataset is minimized, the learning module 18 reaches convergence. The convergence signals the completion of the training.

The system 10 may be configured to be "adaptive" and may be updated periodically after the collection of additional data for the training datasets. In other words, the learning modules 18 may be configured to be "adaptive machine learning" algorithms that are not static and that improve after additional training datasets are collected. In some embodiments, the training network 20 may employ a standalone image bank of crystalline lens structure from the plurality of training ultrasound bio-microscopy images. For example, the training ultrasound bio-microscopy image 300 may include only the structural details of the lens 304.

Figure 7A:
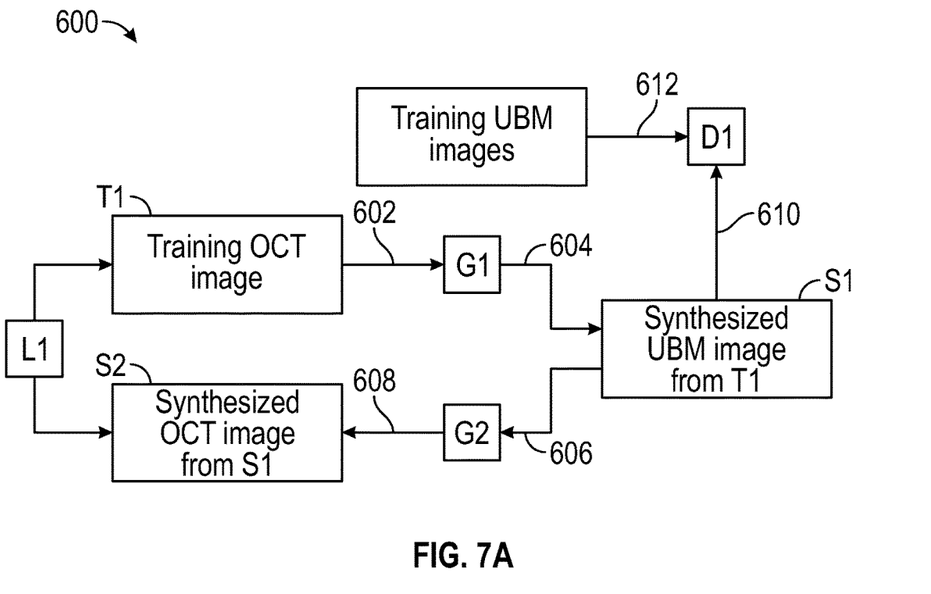
FIG. 7A is a schematic flowchart for an example forward training cycle for the learning modules of FIG. 1, in accordance with a second embodiment.
Figure 7B:
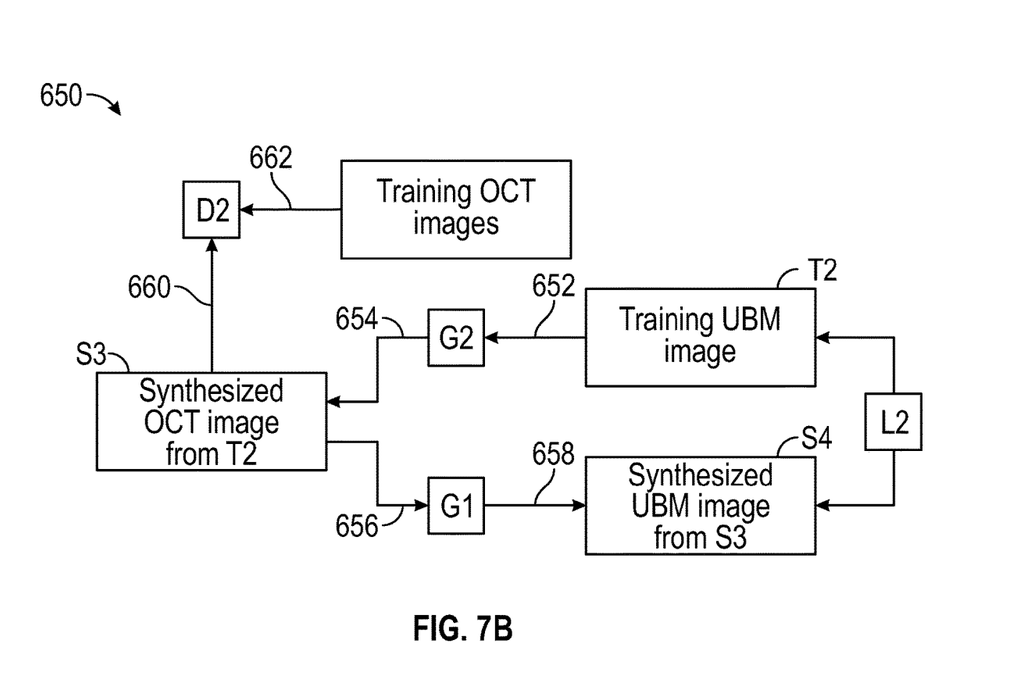
FIG. 7B is a schematic flowchart for an example reverse training cycle for the learning modules of FIG. 1, in accordance with the second embodiment.

In a second embodiment, training network 20 incorporates a cycle generative adversarial network (cycleGAN), an example of which is described in FIGS. 7A and 7B. In this embodiment, the training dataset includes unpaired sets of the plurality of training ultrasound bio-microscopy images and respective training OCT images. In other words, learning modules 18 are adapted to obtain the characteristics of one image domain and determine how these characteristics may be translated into another image domain, all in the absence of any paired training examples.

Referring to FIGS. 7A and 7B, the training network 20 includes a first discriminator D1 and a second discriminator D2. Each of the first generator G1, the second generator G2, the first discriminator D1 and the second discriminator D2 may incorporate separate neural networks with different goals.

The training network 20 is configured to execute a forward training cycle 600 with the first generator G1, the second generator G2 and the first discriminator D1, as shown in FIG. 7A. As shown by arrow 602, a first training OCT image T1 (selected from the respective training OCT images) is inputted into the first generator G1. The first generator G1 translates the first training OCT image T1 into a first synthesized ultrasound bio-microscopy (UBM) image S1, as indicated by arrow 604. Per arrow 606, the first synthesized ultrasound bio-microscopy image S1 is inputted into the second generator G2. The second generator G2 then translates the first synthesized ultrasound bio-microscopy image S1 into a second synthesized OCT image S2, as indicated by arrow 608.

Referring to FIG. 7A, the first synthesized ultrasound bio-microscopy image S1 is inputted into the first discriminator D1, per arrow 610. The plurality of training ultrasound bio-microscopy images (which includes multiple images) are also inputted into the first discriminator D1, per arrow 612. The first discriminator D1 is adapted to distinguish between the first synthesized ultrasound bio-microscopy image S1 and the plurality of training ultrasound bio-microscopy images in the forward training cycle 600.

Referring to FIG. 7A, the training network 20 incorporates a first loss function L1 that minimizes differences between the first training OCT image T1 and the second synthesized OCT image S2. The first loss function L1 tries to capture the difference between the distribution of generated data and the "ground truth." The first loss function L1 may incorporate both adversarial loss and cycle consistency loss and may include, but is not limited to, a minimax function, a least-squares function, a Wasserstein loss function or other suitable function. The first discriminator D1 tries to minimize the first loss function L1 while the first generator G1 tries to maximize the first loss function L1 by synthesizing images that cannot be distinguished from the plurality of training ultrasound bio-microscopy images. At the same time, the second generator G2 tries to maximize this loss by synthesizing images that cannot be distinguished from the respective OCT training images. Additional loss functions may be added based on the application at hand. For example, the generator G1 and the generator G2 may be adapted to minimize the difference in lens diameter 410 between the first training OCT image T1 and the second synthesized OCT image S2.

The training network 20 (see FIG. 1) is configured to execute a reverse training cycle 650 with the first generator G1, the second generator G1 and the second discriminator D2, as shown in FIG. 7B. For synthesis, the reverse training cycle 650 uses the same first generator G1 and second generator G2 from the forward training cycle 600.

As indicated by arrow 652, a second training ultrasound bio-microscopy image T2 (taken from the plurality of training ultrasound bio-microscopy images) is inputted into the second generator G2. The second generator G2 translates the second training ultrasound bio-microscopy image T2 into a third synthesized OCT image S3, per arrow 654. The third synthesized OCT image S3 is inputted into the first generator G1, per arrow 656. The first generator G1 translates the third synthesized OCT image S3 into a fourth synthesized ultrasound bio-microscopy image S4, per arrow 658. Referring to FIG. 7B, the training network 20 incorporates a second loss function L2 minimizing differences between the second training ultrasound bio-microscopy image T2 and the fourth synthesized ultrasound bio-microscopy image S4. The second loss function L2 is analogous to the first loss function L1 and may incorporate both adversarial loss and cycle consistency loss.

The third synthesized OCT image S3 is inputted into the second discriminator D2, per arrow 656. Referring to FIG. 7A, the second discriminator D2 is adapted to distinguish between the third synthesized OCT image S3 (inputted per arrow 660) and the respective training OCT images (inputted per arrow 662) in the reverse training cycle 650. Additional loss functions may be added. For example, the generator G1 and the generator G2 may be adapted to minimize the difference in lens diameter 410 between the second training ultrasound bio-microscopy image T2 and the fourth synthesized ultrasound bio-microscopy image S4. As data are enriched, the newly trained learning modules 18 may be continuously improved such that the augmented OCT image 400 with full crystalline lens structure of the lens 404 becomes more elaborate.

Referring now to block 106 of FIG. 2, controller C is configured to obtain the subject data, i.e., the original OCT image 200 of the eye 12, via the OCT device 14. The controller C may be configured to receive and transmit data through a user interface 32. The user interface 32 may be installed on a smartphone, laptop, tablet, desktop or other electronic device and may include a touch screen interface or I/O device such as a keyboard or mouse. The user interface 32 may be a mobile application. The circuitry and components of a mobile application ("apps") available to those skilled in the art may be employed. The user interface 32 may include an integrated processor and integrated memory.

Per block 108 of FIG. 2, the controller C is configured to execute the (trained) learning modules 18 in order to obtain the augmented OCT image 400. In some embodiments, the learning modules 18 includes a generator G*, with the augmented OCT image 400 generated by executing the generator G* (see FIG. 6). In some embodiments, the learning modules 18 includes a first generator G1 and a second generator G2, with augmented OCT image 400 being generated by executing the first generator G1 and the second generator G2 in sequence. The first generator G1 is adapted to translate the original OCT image 200 of the eye 12 into a respective synthesized ultrasound bio-microscopy image and the second generator G2 is adapted to translate the respective synthesized ultrasound bio-microscopy image into the augmented OCT image 400.

Per block 110 of FIG. 2, the controller C is configured to determine at least one lens parameter based on the augmented OCT image 400. As noted above and referring to FIG. 4, the lens parameters may include a lens capsule profile 408, lens diameter 410 and thickness 412 of the lens 404 along the lens diameter 410. The lens parameters may be outputted to a lens selection module 22. Additionally, per block 112 of FIG. 2, the controller C may be configured to select an intraocular lens 24 based at least partially on the lens parameters determined in block 112.

In summary, the system 10 illustrates a robust way to reconstruct information not available from an original OCT image 200 of the eye 12, by leveraging one or more learning modules 18. The system 10 is adapted to estimate the peripheral portion 206 of the original OCT image 200. The technical benefits include improved power calculation for intraocular lenses 24 and proper selection of accommodative type intraocular lenses 24.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A system comprising:
   a controller having at least one processor and at least one non-transitory, tangible memory on which instructions are recorded for a method for augmenting an original optical coherence tomography ("OCT") image of an eye;
   one or more learning modules selectively executable by the controller;
   wherein the one or more learning modules are trained by a training network with a training dataset having a plurality of training ultrasound bio-microscopy images and respective training OCT images;
   wherein execution of the instructions by the processor causes the controller to obtain the original OCT image of the eye, the original OCT image being captured via an OCT device; and
   wherein the controller is configured to generate an augmented OCT image based in part on the original OCT image by executing the one or more learning modules, the augmented OCT image at least partially extending a peripheral portion of the original OCT image.

2. The system of claim 1, wherein:
   the peripheral portion is posterior to an iris of the eye such that the augmented OCT image enables visualization of one or more structures posterior to the iris.

3. The system of claim 1, wherein:
   the controller is configured to obtain at least one lens parameter based on the augmented OCT image.

4. The system of claim 3, wherein:
   the controller is configured to select an intraocular lens based in part on the at least one lens parameter; and
   the at least one lens parameter include a lens diameter and/or a lens capsule profile.

5. The system of claim 1, wherein:
   the OCT device includes an array of laser beams for illuminating the eye.

6. The system of claim 1, wherein:
   the respective training OCT images are correlated to the plurality of training ultrasound bio-microscopy images, the respective training OCT images and the plurality of training ultrasound bio-microscopy images forming paired sets.

7. The system of claim 6, wherein:
   the one or more learning modules includes a generator trained to generate respective synthesized OCT images based in part on the respective training OCT images;
   the training network is a generative adversarial network having a discriminator; and
   the discriminator is adapted to distinguish between the plurality of training ultrasound bio-microscopy images and the respective synthesized OCT images.

8. The system of claim 1, wherein:
   the respective training OCT images are not correlated to the plurality of training ultrasound bio-microscopy images, the respective training OCT images and the plurality of training ultrasound bio-microscopy images forming unpaired sets; and
   the training network is a generative adversarial network having a first discriminator and a second discriminator.

9. The system of claim 8, wherein:
   the one or more learning modules includes a first generator and a second generator; and the augmented OCT image is generated by executing the first generator and the second generator in sequence, the first generator being adapted to translate the original OCT image of the eye into a respective synthesized UBM image and the second generator being adapted to translate the respective synthesized UBM image into the augmented OCT image.

10. The system of claim 9, wherein:
the training network is configured to execute a forward training cycle with the first generator, the second generator and the first discriminator;
a first training OCT image is inputted into the first generator, the first training OCT image being selected from the respective training OCT images;
the first generator to adapted to translate the first training OCT image into a first synthesized ultrasound bio-microscopy image; and
the second generator is adapted to translate the first synthesized ultrasound bio-microscopy image into a second synthesized OCT image.

11. The system of claim 10, wherein:
the first discriminator is adapted to distinguish between the first synthesized ultrasound bio-microscopy image and the plurality of training ultrasound bio-microscopy images in the forward training cycle; and
the training network incorporates a first loss function minimizing differences between the first training OCT image and the second synthesized OCT image.

12. The system of claim 9, wherein:
the training network is configured to execute a reverse training cycle with the first generator, the second generator and the second discriminator;
a second training ultrasound bio-microscopy image is inputted into the second generator, the second training ultrasound bio-microscopy image being selected from the plurality of training ultrasound bio-microscopy images;
the second generator is configured to translate the second training ultrasound bio-microscopy image into a third synthesized OCT image; and
the first generator is configured to translate the third synthesized OCT image into a fourth synthesized ultrasound bio-microscopy image.

13. The system of claim 12, wherein:
the second discriminator is adapted to distinguish between the third synthesized OCT image and the respective training OCT images in the reverse training cycle; and
the training network incorporates a second loss function minimizing differences between the second training ultrasound bio-microscopy image and the fourth synthesized ultrasound bio-microscopy image.

14. A method for augmenting an original optical coherence tomography ("OCT") image of an eye with a system having a controller with at least one processor and at least one non-transitory, tangible memory, the method comprising:
configuring the controller to selectively execute one or more learning modules;
training one or more learning modules, via a training network with a training dataset having a plurality of training ultrasound bio-microscopy images and respective training OCT images;
capturing the original OCT image of the eye, via an OCT device; and
generating an augmented OCT image based in part on the original OCT image by executing the one or more learning modules, the augmented OCT image at least partially extending a peripheral portion of the original OCT image.

15. The method of claim 14, further comprising:
locating the peripheral portion posterior to an iris of the eye such that the augmented OCT image enables visualization of one or more structures posterior to the iris.

16. The method of claim 14, further comprising:
obtaining at least one lens parameter based on the augmented OCT image, the at least one lens parameter including a lens diameter and/or a lens capsule profile; and
selecting an intraocular lens based in part on the at least one lens parameter.

17. The method of claim 14, wherein capturing the original OCT image of the eye includes:
illuminating the eye with an array of laser beams, via the OCT device.

18. The method of claim 14, further comprising:
composing the training dataset with paired sets of the plurality of training ultrasound bio-microscopy images and the respective training OCT images.

19. The method of claim 14, further comprising:
composing the training dataset with unpaired sets of the plurality of training ultrasound bio-microscopy images and the respective training OCT images.

* * * * *